(12) United States Patent
Bruder et al.

(10) Patent No.: US 7,020,234 B2
(45) Date of Patent: Mar. 28, 2006

(54) METHOD FOR PRODUCING TOMOGRAMS OF A PERIODICALLY MOVING OBJECT WITH THE AID OF A FOCUS DETECTOR COMBINATION

(75) Inventors: Herbert Bruder, Hoechstadt/Aisch (DE); Thomas Flohr, Uehlfeld (DE); Karl Stierstorfer, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 11/042,444

(22) Filed: Jan. 26, 2005

(65) Prior Publication Data
US 2005/0169424 A1 Aug. 4, 2005

(30) Foreign Application Priority Data
Jan. 26, 2004 (DE) .................. 10 2004 003 882

(51) Int. Cl.
*A61B 6/03* (2006.01)
*H05G 1/10* (2006.01)

(52) U.S. Cl. ............................. 378/8; 378/19; 378/95; 378/4

(58) Field of Classification Search .................... 378/4, 378/8, 15, 19–23, 94, 95, 901
See application file for complete search history.

(56) References Cited

U.S. PATENT DOCUMENTS

| 5,802,134 | A * | 9/1998 | Larson et al. .................. 378/4 |
| 6,130,929 | A * | 10/2000 | Saha .............................. 378/4 |
| 6,266,553 | B1 * | 7/2001 | Fluhrer et al. ............. 600/428 |
| 6,504,893 | B1 | 1/2003 | Flohr et al. |
| 6,665,370 | B1 * | 12/2003 | Bruder et al. ................ 378/15 |
| 6,819,736 | B1 | 11/2004 | Bruder et al. |

| 2003/0072419 | A1 | 4/2003 | Bruder et al. |

FOREIGN PATENT DOCUMENTS

| DE | 198 42 238 C2 | 4/2000 |
| DE | 199 57 082 A1 | 8/2001 |
| DE | 101 33 237 A1 | 5/2003 |
| DE | 102 07 623 A1 | 11/2003 |

OTHER PUBLICATIONS

Herbert Bruder et al., "Segmented Cardiac Volume Reconstruction- A Novel Reconstruction Scheme for Multislice Cardiac Spiral CT", SIEMENS, Medical Engineering Group.
H. Bruder et al., "Dynamic Cardiac Volume Imaging Using Area Detectors", SPIE Proceedings Medical Imaging 2003.
Thomas Flohr et al., "Heart Rate Adaptive Optimization of Spatial and Temporal Resolution for Electrocardiogram-Gated Multislice Spiral CT of the Heart", Journal of Computer Assisted Tomography, vol. 25, No. 6, 2001, pp. 907-923.

* cited by examiner

*Primary Examiner*—Edward J. Glick
*Assistant Examiner*—Irakli Kiknadze
(74) *Attorney, Agent, or Firm*—Harness, Dickey & Pierce P.L.C.

(57) ABSTRACT

A method is for improving CT image data from a moving examination object, in particular a beating heart. The method includes moving a focus on a circular track about the examination object, wherein scanning data streams, measured in parallel and in a fashion correlated with one another, are collected from a multirow detector. Further, movement data of the examination object are also collected. Angularly complementary data record elements of the same movement phase are retrospectively selected from a number of movement cycles. The data record elements are then reconstructed and reformatted to form incomplete CT images. Subsequently, the incomplete CT images are added up to form complete CT images.

19 Claims, 7 Drawing Sheets

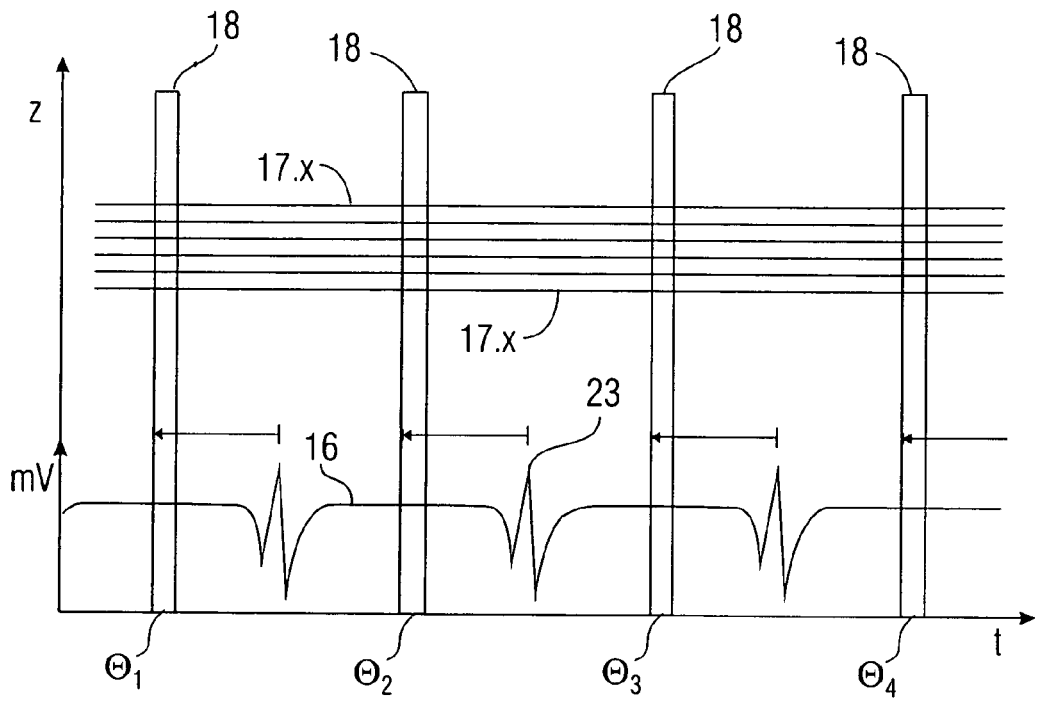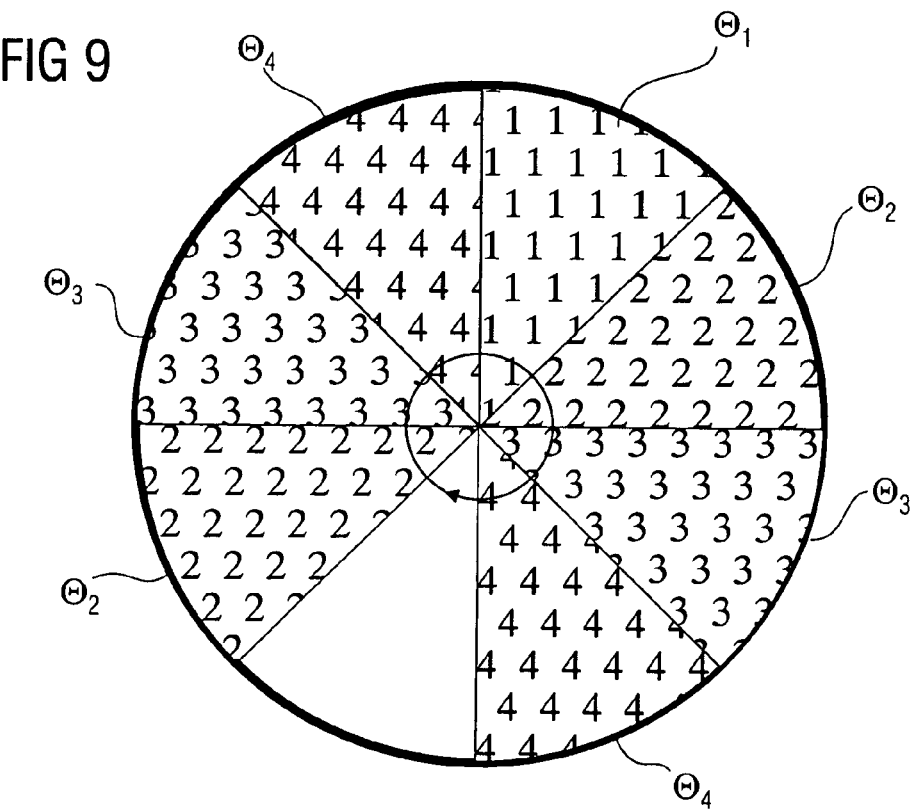

METHOD FOR PRODUCING TOMOGRAMS OF A PERIODICALLY MOVING OBJECT WITH THE AID OF A FOCUS DETECTOR COMBINATION

The present application hereby claims priority under 35 U.S.C. §119 on German patent application numbers DE 10 2004 003 882.1 filed Jan. 26, 2004, the entire contents of which are hereby incorporated herein by reference.

FIELD OF THE INVENTION

The present invention generally relates to a method for producing tomograms. In particular, it relates to a method for producing X-ray CT images of a periodically moving object with periodically recurring cyclic phases. In order to scan the examination object, a focus producing a conical beam is moved with a multirow detector, opposite the focus, on a circular track about the examination object. At the same time, movement signals from the examination object are measured in order to determine movement and rest phases. These are stored in a fashion correlated with the detector output signals.

BACKGROUND OF THE INVENTION

DE 102 07 623 A1, the complete disclosure content of which is expressly incorporated into this application by reference, discloses how there are produced from incomplete spiral data records that include per se only a portion of a 180° segment of a spiral scan, segment images which then lead to complete tomograms through the addition of a number of segment images of a segment stack.

The problem of this known SMPR method, is that although the achieved time resolution is largely adequate for scanning a periodically moving heart, the image quality is inadequate nevertheless because of streaking which cannot be completely removed.

SUMMARY OF THE INVENTION

An object of an embodiment of the present invention is therefore to provide a method for producing tomograms of periodically moving examination objects having an improved image quality. At the same time, a tomography machine suitable therefor is also to be proposed.

The inventors have realized that in order to improve the image quality, it can be advantageous to make use of the method, known per se from DE 102 07 623 A1, of Segmented Multiple Plane Reconstruction of a spiral scan also for circular scanning. In this method, no table feed is executed, in conjunction with a large-area multirow detector. If the detector is of adequate width, the scanning volume of a circuit can suffice to enable a largely complete display of a moving heart, the reconstruction taking place on the basis of a known 2D method. However, in this case an adequate time resolution for displaying the heart also requires the data that are used for the display to be collected from a number of movement periods in a rest phase.

In accordance with the method according to an embodiment of the invention, multilayer projections can be measured sequentially in parallel with recording the patient ECG in a number of consecutive cardiac cycles. The sequentially measured data stream can in this case be divided per revolution into $N_{seg}$ disjoint data segments, it being possible to define in each data segment an image stack (booklet) of inclined reconstruction layers (pages). The center of each data segment can be determined in this case by an appropriate reference projection angle $\Phi_{ref}$. The planes in the respective reference projection angle are attached to the circular track and are inclined with reference to the N-row detector such that when reconstructing M equidistant reconstruction layers all the detector data are used as soon as the number of equidistant reconstruction layers is greater than or equal to the number of detector rows of the multirow detector.

It is possible in general for the reconstruction layers also to be of curved shape. After the reconstruction of the segment image stack, it is possible to carry out reformatting to the desired target image planes of uniform orientation segment by segment in the direction of the system axis. A weighting method known per se, for example, can be used for this purpose.

Since the measured data of the multirow detector are assigned uniquely to the measured movement data of the moving object, there is also a unique assignment between the movement situation of the observed examination object, preferably the heart phases in the ECG, and the reformatted segment image stacks. As such, the image layers of the segment image stacks can now be summed up in relation to a specific cyclic phase, or a selected heart phase, for example a rest phase, to form a complete CT image, this being done in correct phase sequence.

The following situation results when considering the special case of a two-segment reconstruction on a heart in the case of which segments of two consecutive cardiac cycles are used for image construction:

A data interval of length $\theta_{scan} \geq \pi$ is composed of sectors obtained in two successive cardiac cycles, the sectors $s_1$ and $s_2$ being determined such that they supplement one another in a complementary fashion to form a data interval of length $\theta_{scan}$. In this process, the temporal position in the successive cardiac cycles is to be determined exactly in phase. Segments $s_1$, $s_2$ of different lengths are generally yielded thereby.

To construct the respective image volume, the image stacks (booklets) separately determined for each data segment are reconstructed and reformatted, and subsequently added up layer by layer to form a complete CT image.

The time resolution $\Delta t$ is dependent here on the local heart rate, and in the most favorable case is $$\Delta t = \frac{\theta_{scan}}{4\pi} \cdot T_{rot},$$

in conjunction with an equal length of the two sectors $s_1$ and $s_2$, with $T_{rot}$ being the time for a complete circuit of the focus. In the most unfavorable case, the time resolution is $$\Delta t = \frac{\theta_{scan}}{2\pi} \cdot T_{rot},$$

because in this case one of the two sectors is of length zero.

In the case of triggered recordings for which the X radiation is switched on and off or varied depending on the situation, a data stream of length $\theta_{scan}$ is scanned only in relation to a selected heart phase. This data stream can then be divided into $N_{seg}$ disjoint segments in the way specified above, a segment image stack being defined in the above sense in each of these segments. Each segment image stack is then separately reconstructed and reformatted to give new segment image stacks of uniform orientation, preferably in axial layers. It is then necessary for corresponding segment tomograms to be added to form a complete CT image for the purpose of layerwise image calculation.

On the basis of these fundamental statements, the inventors propose, in one embodiment, a method for producing tomograms, in particular X-ray CT images, of a periodically moving examination object with periodically recurring cyclic phases that has at least the following method steps:

in order to scan the examination object, a focus producing a conical beam (conical=formed in the shape of a fan in two mutually perpendicular planes) is moved with a multirow detector, opposite the focus, on a circular track about the examination object and scanned in a sectorwise fashion, the individual sectors sweeping an angle of less than 180°, and the beam is spread out so wide that the volume of the moving examination object is completely covered by circular scanning without additional lateral movement, at the same time, movement signals of the moving object are measured for the purpose of detecting a cyclic phase to be considered or a cyclic phase interval and are stored, the temporal correlation between the movement data and the detector output data also being stored, subsequently, segment image stacks are reconstructed independently of one another with the aid of the detector output data stored in a sectorwise fashion, and axial segment images are reformatted therefrom, whereupon complete CT tomograms that are layerwise angularly complementary and supplement one another to form 180° are summed up per detector row from the axial and incomplete segment images, and use being made only of detector output data from sectors that were scanned in the cyclic phase to be considered or in the cyclic phase interval to be considered.

It is preferable here to use detector output data from a number of successive cycles in order to achieve a correspondingly high time resolution. Furthermore, a heart of a living being, preferably a patient with periodically alternating movement and rest phases is mostly scanned as cyclically moving examination object, in which case as movement signals the ECG signals from the heart, for example, for the detection of the cyclic phase, preferably for the detection of movement and/or rest phases, are measured. It should be pointed out in this case that, although it is mostly only the rest phases of the heart that are considered, it is also possible with increasing rotational speed for the focus to consider other cyclic phases of the heart or generally of an examination object for which the examination object is in acute movement. It is thereby even possible to produce image sequences over the entire cycle.

Thus, scanned data streams are collected in parallel and in a fashion correlated with one another from the multirow detector and movement data, angularly complementary data record elements of the same cyclic phase are retrospectively selected from a number of movement cycles, the data record elements are reconstructed and reformatted to form incomplete CT images, and subsequently the incomplete and axially reformatted CT images are added up to form complete CT images.

According to an embodiment of the invention, parallel rebinning, preferably a line by line parallel rebinning, can be carried out before the back-projection.

The rotation time $T_{Rot}$ of the focus can advantageously be set in such a way that subsegments, of equal length and supplementing one another seamlessly, from a number of successive cyclic phases of the movement periods are added up to form complete CT images. This achieves an always maximum time resolution.

It is advantageous, furthermore, when segment image stacks are respectively formed for M equidistant reconstruction layers from the detector data, in which case it holds that $M \geq N$, where N is the number of detector rows, and reformatting is carried out on parallel and equidistant image planes.

Moreover, in order to reduce the dose commitment of the examination object, it is also possible to switch off or at least reduce the radiation that emanates from at least one focus over at least the greater part of the movement phase, in a fashion controlled indirectly or directly, by the measured movement signals.

Overall, the method according to an embodiment of the invention shows that it is advantageously possible to obtain improved CT image data from a moving object, in particular a beating heart, in that a focus is moved on a circular track about the object and scanned data streams, measured in parallel and in a fashion correlated with one another, from a large multirow detector and movement data of the object are collected, angularly complementary data record elements of the same movement phase are retrospectively selected from a number of movement cycles, the data record elements are reconstructed to form incomplete CT images, reformatted, and subsequently the incomplete CT images are added up to form complete CT images.

BRIEF DESCRIPTION OF THE DRAWINGS

The invention is described in more detail below with the aid of preferred exemplary embodiments and the figures, the following reference symbols being used. 1: CT unit; 2: X-ray tube; 3: Multirow detector; 4: Patient couch; 5: System axis/z-axis; 6: Gantry; 7: Patient; 8: ECG measuring line; 9: Control/Measuring line; 10: Control/Evaluation unit; 11: Display screen; 12: Keyboard; 13: Focus; 14: Beam; 15: Heart; 16: ECG line; 17.x: Section planes; 18: Rest phase; 19: Circular track of the focus; 20.x: Ray planes; 21.x: Parallel rays; 22: Physical detector; 23: R wave; 24: Start of the rest phase; m: Number of detector rows; n: Number of detector elements per detector row; $P_x$: Program module; $T_{rot}$: Rotation time; $\Theta_1$: 1st scanning sector; $\Theta_2$: 2nd complementary scanning sector; $\Theta_3$: 3rd complementary scanning sector; $\Theta_4$: 4th complementary scanning sector.

In detail, in the figures:

FIG. 8: shows an illustration of the scanning method according to an embodiment of the invention with sectorwise data collection over 4 heart periods;

FIG. 9: shows a schematic of a possible sector combination for complete CT images with data collection in 4 sectors of equal length over 4 periods.

DETAILED DESCRIPTION OF THE EXEMPLARY EMBODIMENTS

Figure 1:
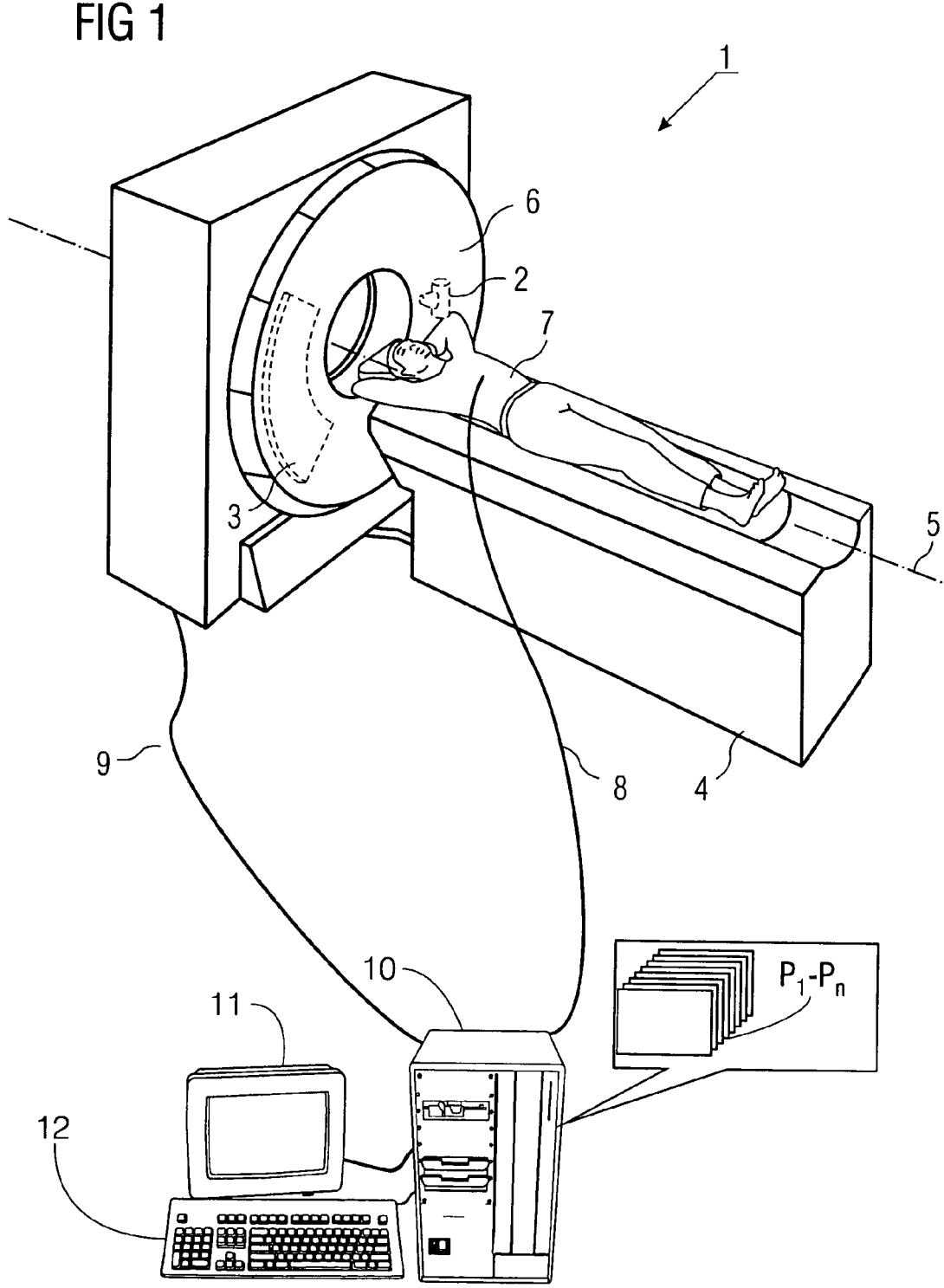
FIG. 1: shows an illustration of a computer tomograph.

FIG. 1 shows a computer tomograph 1 having a gantry 6 in which a circularly revolving X-ray tube 2 with an opposite multirow detector 3 is located. Also illustrated is a patient 7 who is lying on a patient couch 4 and is moved into the opening of the CT 1 for the scanning operation, there being no movement of the focus in the direction of the system axis 5 during the scanning operation, in which the X-ray tube is moved in a circle about the patient. The computer tomograph 1 is controlled by the control and evaluation unit 10 via the control/measuring line 9 over which the data collected by the multirow detector 3 are also transmitted.

Integrated furthermore in the control and evaluation unit 10 is an ECG that measures the potential currents caused by the heart via the ECG measuring line 8 in order to detect the movement situation of the heart at any one time or to determine the respective cyclic phases. The control and evaluation unit 10 has internal memories and arithmetic processors via which the programs $P_1$ to $P_n$ for controlling the computer tomograph and for evaluating the collected data are run. Moreover, a keyboard 12 for data input and a monitor 11 for displaying data are connected to the control and evaluation unit.

Figure 2:
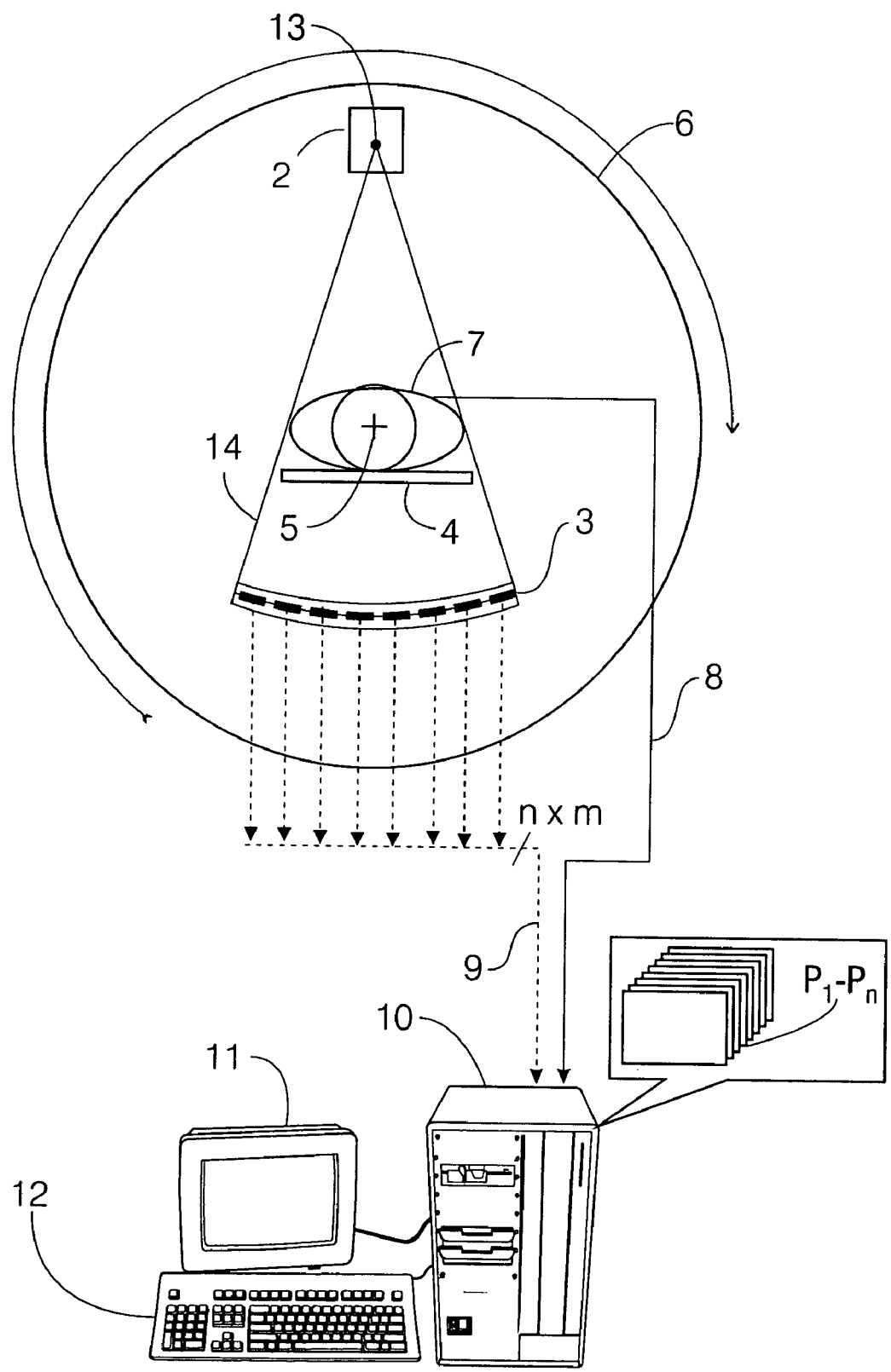
FIG. 2: shows a schematic of a computer tomograph in cross section.

FIG. 2 shows the computer tomograph of FIG. 1 in cross section and in a schematic. Located inside the X-ray tube 2 is a focus 13 from which a beam 14 expanded into a fan emanates and strikes the opposite multi-row detector 3. Upon passage of the X radiation through the patient 7, the X-rays are attenuated differently in accordance with the tissue struck right through, and the attenuation is measured by the individual detectors of the detector in an n×m-row matrix, and passed on to the control and evaluation unit 10 via the measuring line 9. According to an embodiment of the invention, position data relating to the current rotary position of the gantry 6 and also the ECG data via the ECG measuring line 8 are also stored indirectly or directly during the measurement operation in the control and evaluation unit 10.

Figure 3:
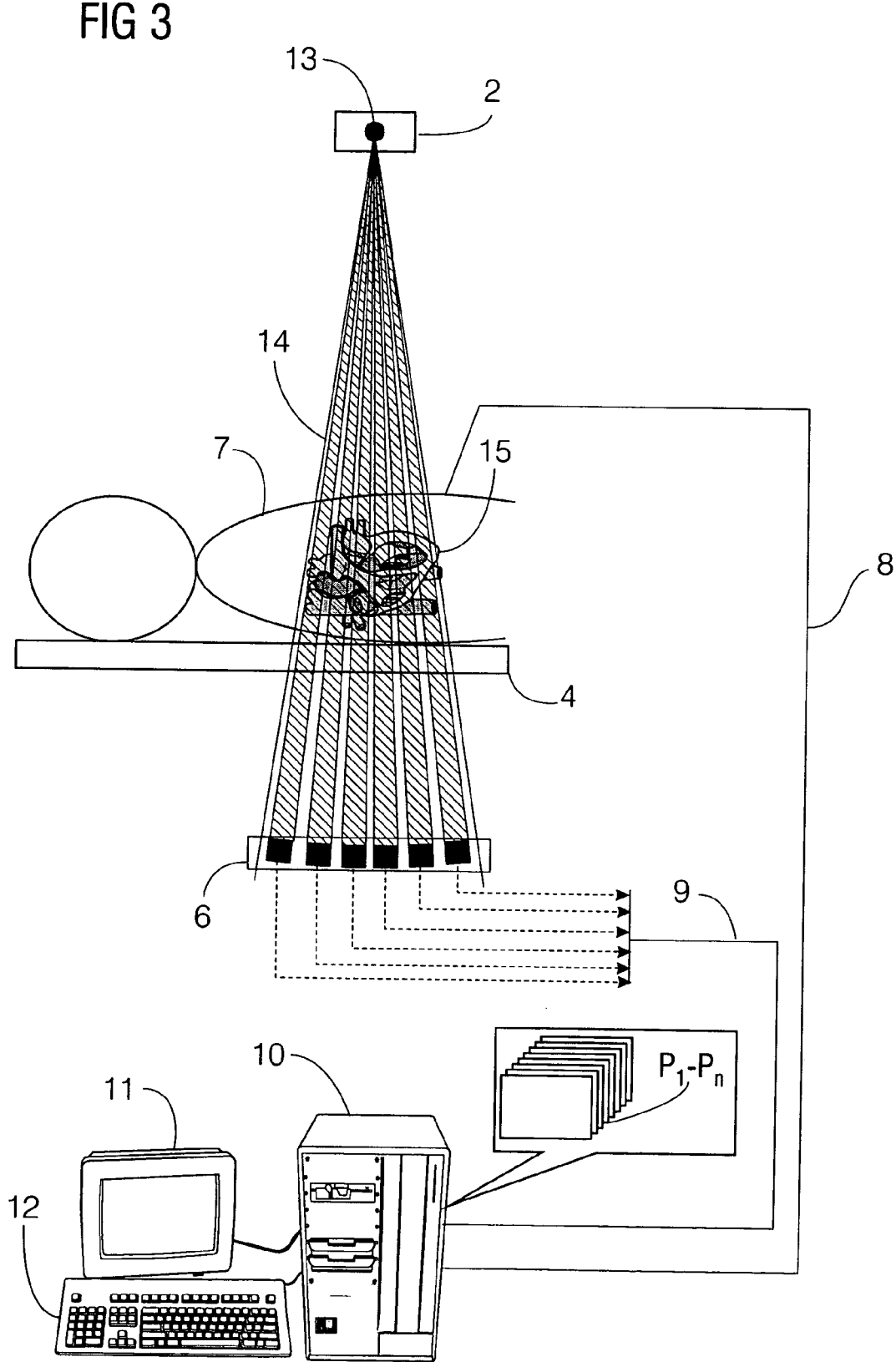
FIG. 3: shows a schematic of a computer tomograph in longitudinal section.

FIG. 3 once again shows the computed tomography unit 1 from FIG. 1, but this time in longitudinal section. Here, the trans-irradiation of a heart 15 beating in the patient 7 is demonstrated schematically. For reasons of clarity, only one detector has been illustrated in FIGS. 2 and 3 with a few rows and a few detector elements per row. However, according to an embodiment of the invention these are multirow detectors that have a large number of detector rows and detector elements per detector row so that at least the moving heart can be completely scanned with a single circular scanning operation without simultaneously feeding the patient in the direction of the system axis.

Figure 4:
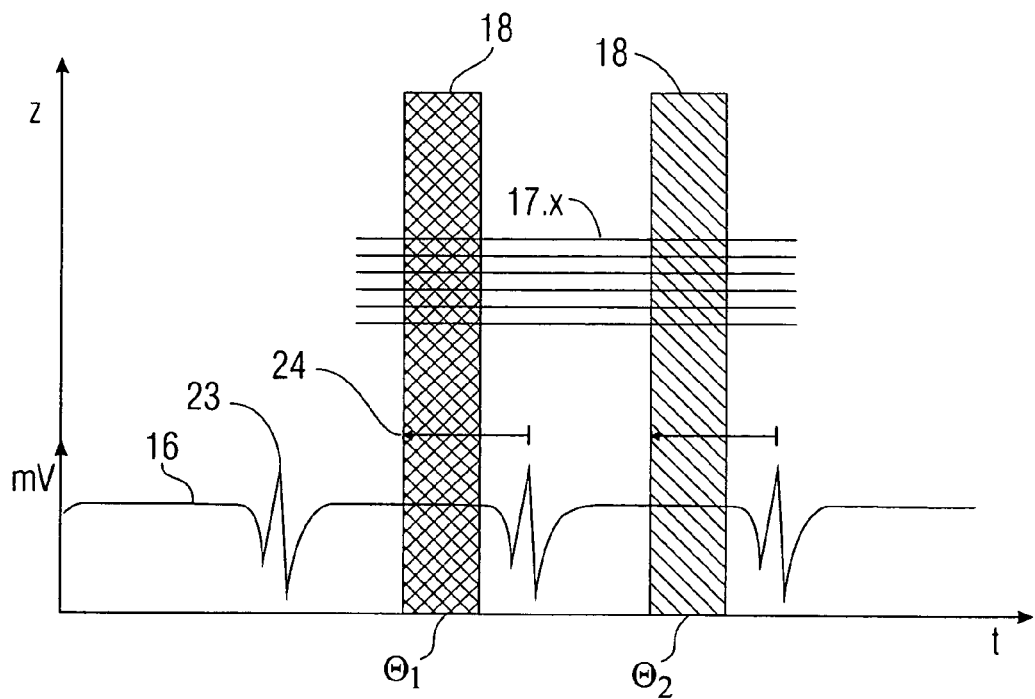
FIG. 4: shows an illustration of the scanning method according to an embodiment of the invention with sectorwise data collection over 2 heart periods.

FIG. 4 shows a schematic of the time profile of an inventive circular scanning operation of a heart. Here, the time axis is illustrated on the abscissa, while the ordinate on the one hand shows the system axis or z-axis, and on the other hand shows the measured cardiac activity of the ECG recorder in millivolts.

The ECG line bears the reference symbol 16, the start of the rest phase 24 being determined according to an embodiment of the invention in a retrospective fashion on the basis of the R wave 23. The rest phase itself is illustrated in the bar 18. A number of sequential heartbeat periods are used to evaluate CT images in the section planes 17.x. A total of four heart periods are illustrated in FIG. 4, two juxtaposed heart periods being used with two rest phases 18 for collecting the data.

Figure 5:
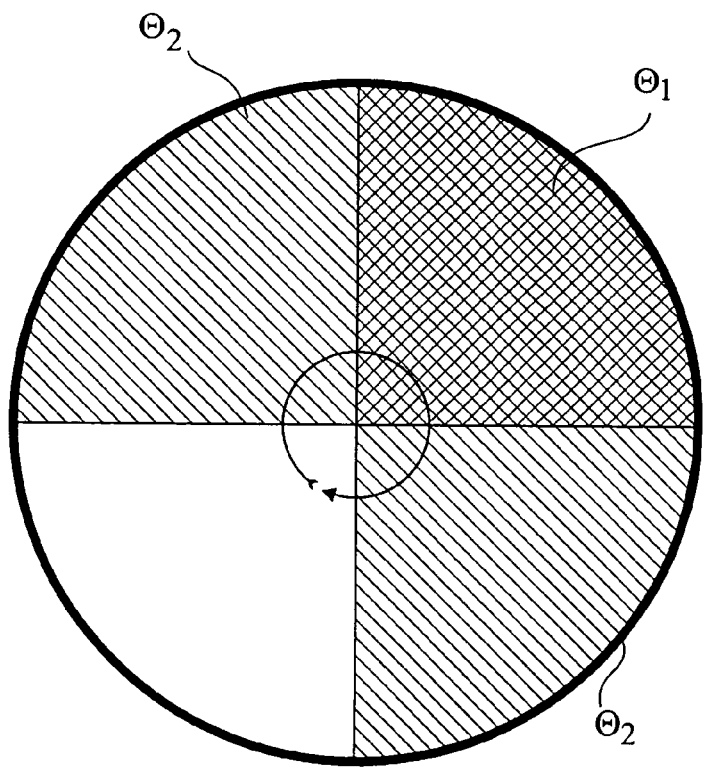
FIG. 5: shows a schematic of a possible sector combination for complete CT images with data collection in 2 sectors of equal length over 2 heart periods.

The sectorwise data collection is illustrated in FIG. 5. Here, the focus or beam traverses a first circle sector $\Theta_1$ during the first rest phase 18, and a second circle sector $\Theta_2$ in the subsequent rest phase 18. Ideally, the rate of rotation of the focus is set in this case such that both sectors each cover 90° and, as illustrated in FIG. 5, supplement one another in a complementary fashion such that overall a complete sector of at least 180° is scanned. Use may be made as desired for this purpose either of the second circle sector $\Theta_2$ lying directly after, or that lying directly in front of, the first circle sector $\Theta_1$.

Figure 6:
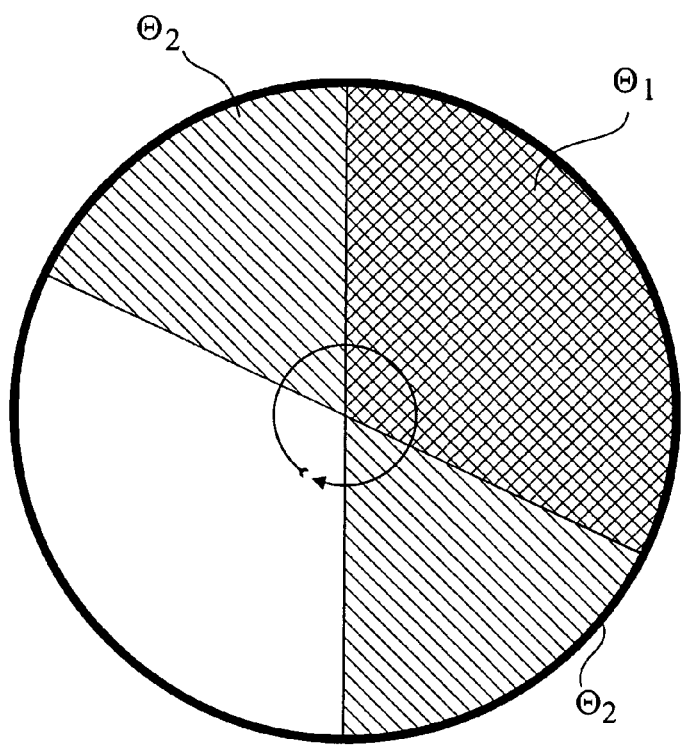
FIG. 6: shows a schematic of a possible sector combination for complete CT images with data collection in 2 sectors of different length over 2 periods.

The data collection can be performed in accordance with the situation illustrated in FIG. 6 for the case of non-optimum correspondence between the rotation time of the gantry and the heart rate. Here, the rate of rotation is set relatively high such that the first circle sector $\Theta_1$ sweeps an angle of over 90°. Use is then correspondingly made of an adjacent angle of less than 90° for the second circle sector $\Theta_2$ such that overall a complete half revolution is measured again.

Figure 7:
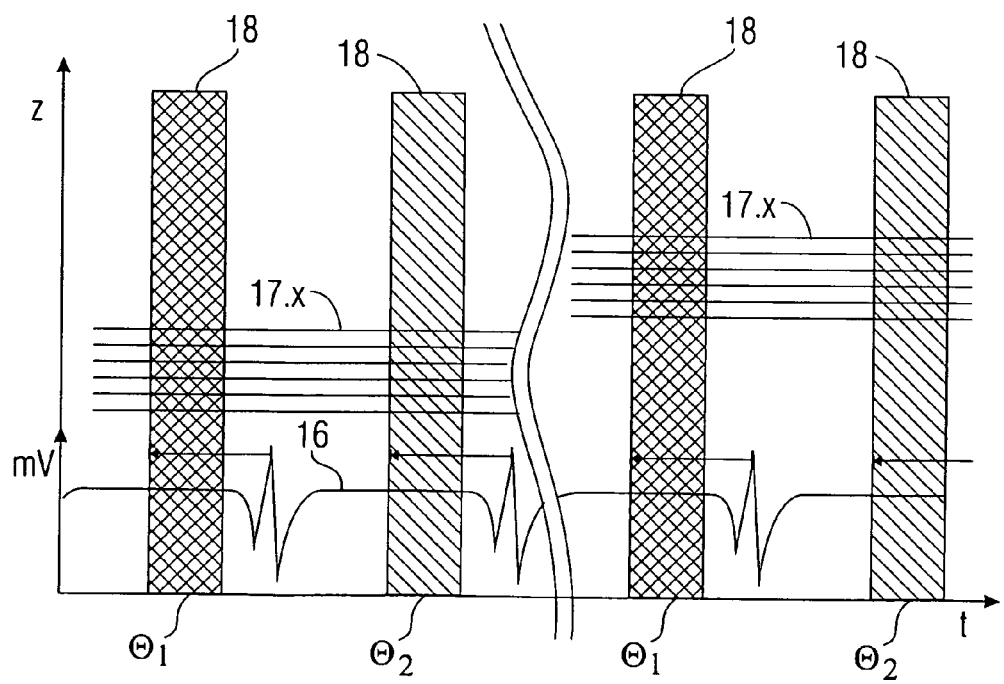
FIG. 7: shows an illustration of the scanning method according to an embodiment of the invention for the case of sequential scanning with feed in the z-direction.

For the case in which the object to be examined cannot be completely scanned by a single circular scan despite the wide expansion of the scanning beam and the large extent of the multirow detector in the direction of the z-axis, it is also possible for a number of circular scans according to the invention to be juxtaposed sequentially, and to feed in the direction of the system axis between the individual scans. FIG. 7 shows a schematic of such an operation.

A further increase in the time resolution is illustrated in FIGS. 8 and 9. These figures show scanning over 4 heart periods and 4 circle sectors $\Theta_{1-\Theta4}$. In accordance with the multiplication of the scanning sectors, the time span covered within the rest phase is also smaller, and can thereby be fitted even more effectively into a heart phase that is actually motionless, so that the image quality can be substantially improved on the basis of the higher time resolution. The higher time resolution not only renders it possible to obtain recordings from rest phases, but also enables images to be obtained from any desired cyclic phases, which can also constitute heartbeats.

FIG. 8 is a schematic of the scanning according to the invention with sectorwise data collection over 4 heart periods, whereas FIG. 9 shows the possible complementary assemblage of sectors that is required in order to obtain complete CT images by addition from the individual incomplete CT images that have been reconstructed and reformatted from the data of the complementary sectors.

Figure 10:
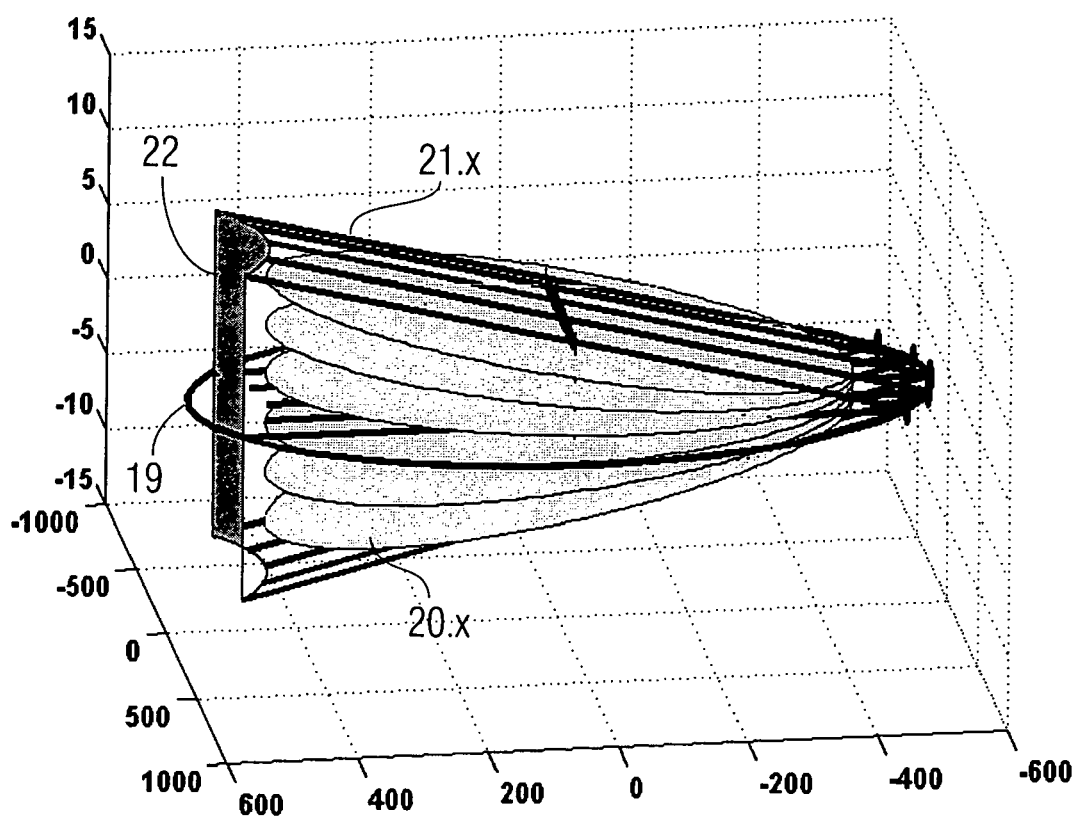
FIG. 10: shows a schematic of a stack of reconstruction layers in parallel geometry in the case of circular scanning.

FIG. 10 shows a stack of non-axial reconstruction layers in parallel geometry in the case of circular scanning of a sector. Only six fan-shaped reconstruction layers are shown here, as well, for the purpose of a clear illustration. The reconstruction segment is only a fraction of the complete revolution for each stack. It is also clearly to be seen here that the physical detector 22 is concavely curved in accordance with the parallel rebinning.

As illustrated in FIG. 10, in all the data collection methods illustrated above, such fan-shaped image stacks 20.1–20.n that are subsequently reformatted to yield axial image layers in a way known per se are reconstructed according to the invention from each of the scanning sectors. These axial images do not constitute a complete representation of a section of the object under examination. In order to obtain a complete image, it is necessary, in addition, to use the data packet of the second complementary sector to calculate, likewise in the same way, incomplete tomograms so that these can subsequently be added up and yield a recognizable tomogram on the basis of their information content, which is complete overall, over an entire semicircular sector.

It may be noted in addition that the circle sectors used need not necessarily be the same size, but that it is also possible to use sectors of different size as long as the images added up at the end consist of complementary sectors covering 180° overall. In order to improve the time resolution, it can be advantageous in part to collect data not only over two heart periods but over three or four heart periods, it being possible for the use of an excessively large number of heart periods to lead, in turn, to fuzziness.

Thus, overall, an embodiment of the invention represents a method and a computed tomograph in which high-resolution CT images are produced by circular scanning of a moving object by virtue of the fact that subsegments are scanned in a number of successive rest phases, and the subsegments are respectively reconstructed and reformatted per se in order subsequently to add up a number of tomograms of the subsegments, the sum of the subsegments reproducing overall a complementary half segment of a circular revolution of the focus about the examination object.

Exemplary embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for producing tomograms of a periodically moving examination object with periodically recurring cyclic phases, comprising:
   moving a focus producing a conical beam to scan the examination object, a multirow detector existing opposite the focus on a circular track about the examination object, wherein the examination object is scanned in a sectorwise fashion with individual sectors sweeping at an angle of less than 180°, and wherein the beam is spread out such that the volume of the moving examination object is completely covered by circular scanning without additional lateral movement;
   measuring, at the same time, movement signals from the moving examination object to determine and store a cyclic phase or a cyclic phase interval, wherein a temporal correlation between the movement data and the detector output data is also stored;
   reconstructing segment image stacks, independently of one another with the aid of the detector output data stored in a sectorwise fashion, wherein incomplete axial segment images are reformatted therefrom;
   summing up complete CT tomograms, layerwise angularly complementary and supplementing one another to form 180°, per detector row from the axial and incomplete segment images, wherein detector output data from sectors that were scanned in the determined cyclic phase or in the determined cyclic phase interval are used.

2. The method as claimed in claim 1, wherein detector output data from a number of successive cycles are used.

3. The method as claimed in claim 2, wherein parallel rebinning is carried out before the back-projection.

4. The method as claimed in the preceding patent claim 3, wherein the parallel rebinning is carried out line by line.

5. The method as claimed in claim 2, wherein segment image stacks are respectively formed for M equidistant reconstruction layers from the detector data, in which case it holds that $M \geq N$, where N is the number of detector rows, and reformatting is carried out on parallel and equidistant image planes.

6. The method as claimed in claim 1, wherein a heart of a living being, with periodically alternating movement and rest phases, is scanned as cyclically moving examination object.

7. The method as claimed in claim 6, wherein as movement signals ECG signals from the heart for the detection of the cyclic phase are measured.

8. The method as claimed in claim 6, wherein, in order to reduce the dose commitment of the patient, the radiation that emanates from the focus is switched off or reduced over at least the greater part of the movement phase in accordance with the measured movement signals.

9. The method as claimed in claim 6, wherein as movement signals ECG signals from the heart for the detection of the cyclic phase, for the detection of at least one of movement and rest phases, are measured.

10. The method as claimed in claim 6, wherein parallel rebinning is carried out before the back-projection.

11. The method as claimed in claim 10, wherein the parallel rebinning is carried out line by line.

12. The method as claimed in claim 6, wherein segment image stacks are respectively formed for M equidistant reconstruction layers from the detector data, in which case it holds that $M \geq N$, where N is the number of detector rows, and reformatting is carried out on parallel and equidistant image planes.

13. The method as claimed in claim 1, wherein parallel rebinning is carried out before the back-projection.

14. The method as claimed in claim 13, wherein the parallel rebinning is carried out line by line.

15. The method as claimed in claim 1, wherein the rotation time of the focus is set in such a way that subsegments, of equal length and supplementing one another seamlessly, from a number of successive cyclic phases of the movement periods are added up to form complete CT images.

16. The method as claimed in claim 1, wherein segment image stacks are respectively formed for M equidistant reconstruction layers from the detector data, in which case it holds that $M \geq N$, where N is the number of detector rows, and reformatting is carried out on parallel and equidistant image planes.

17. The method as claimed in claim 1, wherein the method is for producing tomograms of X-ray CT images.

18. A computed tomography unit for producing tomograms of an at least partially periodically moving examination object with periodically recurring cyclic phases, comprising:
   a focus for scanning the examination object, which produces a conical beam; and
   a multirow detector opposite the focus, at least the focus being movably arranged on a circular track about the examination object;
   storage means for collecting detector output data that represent the attenuation of rays emanating from the focus upon passage through the examination object, together with spatial orientation data of the rays;

acquisition and storage means for simultaneously collecting movement signals from the examination object in order to detect a cyclic phase or a cyclic phase interval, and for storing temporal correlation between the movement data and the detector output data; and means for retrospectively combining the detector output signals from individual subsegments per detector row that together respectively produce a complete segment sweeping at least 180° and represent a rest phase of the moving examination object.

19. The computed tomography unit as claimed in claim 18, wherein the beam is spread out such that the volume of the moving examination object is completely coverable by circular scanning without additional lateral movement.

* * * * *